(12) United States Patent
Davoine

(10) Patent No.: US 11,771,857 B2
(45) Date of Patent: Oct. 3, 2023

(54) PROTECTIVE COVER FOR A MEDICAL VENTILATOR THAT CAN BE USED IN A CONTAMINATED ENVIRONMENT OF THE NRBC TYPE

(71) Applicant: Air Liquide Medical Systems, Antony (FR)

(72) Inventor: Romain Davoine, Grenoble (FR)

(73) Assignee: Air Liquide Medical Systems, Antony (FR)

( * ) Notice: Subject to any disclaimer, the term of this patent is extended or adjusted under 35 U.S.C. 154(b) by 763 days.

(21) Appl. No.: 16/899,662

(22) Filed: Jun. 12, 2020

(65) Prior Publication Data

US 2020/0390990 A1 Dec. 17, 2020

(30) Foreign Application Priority Data

Jun. 14, 2019 (FR) ...................................... 1906359

(51) Int. Cl.
*A61M 16/00* (2006.01)
*A61M 16/08* (2006.01)
*A61M 16/06* (2006.01)
*A61M 16/20* (2006.01)

(52) U.S. Cl.
CPC ........ *A61M 16/0087* (2013.01); *A61M 16/06* (2013.01); *A61M 16/0816* (2013.01); *A61M 16/0883* (2014.02); *A61M 16/208* (2013.01); *A61M 2202/0208* (2013.01); *A61M 2209/06* (2013.01)

(58) Field of Classification Search
CPC ................ A61M 16/00; A61M 16/003; A61M 16/0057; A61M 16/0087; A61M 16/06; A61M 16/08; A61M 16/0883; A61M 16/0816; A61M 16/20; A61M 16/208; A61M 2202/0208; A61M 2205/0205; A61M 2205/0238; A61M 2209/06
See application file for complete search history.

(56) References Cited

U.S. PATENT DOCUMENTS

| 5,458,132 A | 10/1995 | Yabe et al. | |
| 7,731,575 B2 * | 6/2010 | Ozil .......................... | A62B 7/10 454/283 |
| 2007/0017510 A1 * | 1/2007 | Riedo ....................... | A62C 4/00 128/201.25 |
| 2012/0080040 A1 | 4/2012 | Skora et al. | |

FOREIGN PATENT DOCUMENTS

FR 3 034 677 10/2016

OTHER PUBLICATIONS

French Search Report for corresponding FR 1906359, dated Feb. 17, 2020.

* cited by examiner

*Primary Examiner* — Colin W Stuart
(74) *Attorney, Agent, or Firm* — Allen E. White

(57) ABSTRACT

The invention relates to a protective cover (1) for a medical ventilator (20) adapted for use in a contaminated environment, in particular an NRBC environment, having a peripheral casing (2) defining an internal compartment (3) designed to accommodate a medical ventilator (20). The peripheral casing (2) has a plurality of connection interfaces (4, 5, 6, 7) sealably attached to said peripheral casing (2). Each connection interface (4, 5, 6, 7) has at least one internal gas passage with at least one gas inlet and at least one gas outlet. A sealing device is arranged in the internal gas passage of at least one connection interface (4, 5, 6, 7) for sealing said internal gas passage.

10 Claims, 2 Drawing Sheets

PROTECTIVE COVER FOR A MEDICAL VENTILATOR THAT CAN BE USED IN A CONTAMINATED ENVIRONMENT OF THE NRBC TYPE

CROSS REFERENCE TO RELATED APPLICATIONS

This application claims the benefit of priority under 35 U.S.C. § 119 (a) and (b) to French Patent Application No. 1906359, filed Jun. 14, 2019, the entire contents of which are incorporated herein by reference.

BACKGROUND

The invention relates to a protective cover and to a medical ventilator equipped with such a protective cover that can be used for emergency treatment of a patient suffering from respiratory failure in a contaminated NRBC type environment, particularly in the event of a conflict, an attack or an industrial accident.

In a hospital or in the field, the emergency treatment of a patient suffering from respiratory failure can be performed using a breathing assistance apparatus, commonly called medical ventilator, supplying ambient air, optionally enriched with oxygen originating from a gas bottle or similar.

Ideally, a medical ventilator must be able to be used irrespective of the situation and/or the location in which the patient is found, including in a contaminated environment of the nuclear, radiological, biological and/or chemical (or NRBC) type, for example, in the event of a conflict, an attack or an industrial accident, i.e. for civil and/or military interventions/uses.

In an NRBC-type contaminated environment, the ambient air is contaminated and therefore must be purified, typically filtered, before being administered to the patient by means of the medical ventilator.

However, in practice, a medical ventilator that has been used in an NRBC environment is generally subsequently discarded and destroyed since it is very difficult, even impossible, for it to be totally and/or effectively disinfected or decontaminated, particularly due to contaminated particles, for example, chemical, biological or radioactive products that can penetrate every corner of the ventilator.

Bearing in mind that it is also often necessary for several different ventilators to be used between the interventions and/or changes of patients treated in these contaminated environments, in particular of the NRBC type, it is easy to understand that discarding these devices is unsatisfactory, since it involves "wasting" contaminated ventilators, also bearing in mind that they still operate perfectly.

The stated problem therefore is that of being able to medically assist a patient in a contaminated environment, in particular of the NRBC type, suffering from respiratory failure and to do so without involving the systematic discarding of the medical ventilator used to this end, and by even allowing it to be subsequently reused.

SUMMARY

The solution of the invention is a protective cover for a medical ventilator, i.e. a breathing assistance apparatus, adapted for use in a contaminated environment, in particular an NRBC environment, comprising a peripheral casing defining an internal compartment designed to accommodate a medical ventilator, characterized in that:

the peripheral casing comprises a plurality of connection interfaces sealably attached to said peripheral casing, comprising:
  a first connection interface allowing fluid connection of a patient circuit; and
  a second connection interface allowing fluid connection of an air purification device, typically a filtration device;
and each connection interface comprises at least one internal gas passage with at least one gas inlet and at least one gas outlet.

According to the considered embodiment, the protective cover for a medical ventilator of the invention can comprise one or more of the following features:

at least one sealing device is arranged in the internal gas passage of at least one connection interface for sealing said internal gas passage normally, i.e. in the absence of any connection to the considered connection interface;
preferably, a sealing device is arranged in each internal passage of the connection interfaces;
at least one sealing device arranged in at least one internal gas passage is a non-return valve;
each non-return valve is normally closed to prevent contaminated air from entering the internal gas passage in which said non-return valve is arranged. The one or more valves are only opened when the inlet and/or the outlet of the one or more connection interfaces is/are connected.
according to another embodiment, a plug or detachable lid sealably seals the inlet of the internal gas passage of at least one connection interface;
at least one portion of the peripheral casing is formed by at least one transparent polymer material, preferably PVC;
at least one portion of the peripheral casing is flexible, preferably it comprises a flexible casing wall that is less than or equal to approximately 0.5 mm thick;
it comprises a third connection interface allowing fluid connection of a PEP pressure control line, i.e. PEP pressurization (i.e. Positive Expiratory Pressure);
it comprises a fourth connection interface allowing fluid connection of an oxygen supply line, in particular of a flexible pipe supplied with oxygen supplied by an oxygen container, such as an oxygen bottle;
each connection interface comprises an interface body traversed by an internal gas passage fluidly connecting the inside and the outside of the peripheral casing;
each connection interface comprises an internal gas passage;
the connection interfaces, i.e. the interface bodies, are at least partly formed by at least one semi-rigid material;
said at least one semi-rigid material is selected from thermoplastic polymers, for example, of the ABS or PA type, and elastomers, for example, of the thermoplastic, polyurethane or silicon type;
it comprises opening/closing means allowing access to be granted to the internal compartment, i.e. the internal volume, of the cover for the insertion or extraction of a medical ventilator;
the opening/closing means comprise a slide fastener or a zip or similar closure, in particular one or more hook-and-loop strips of the Velcro™ type;
the opening/closing means are designed to allow hermetic closure of the cover;
it is sealed, i.e. pollutants cannot enter therein, when the cover is hermetically closed;

the smooth surface of the cover is designed to repel liquids and/or to prevent the adhesion of solid particles, for example, it can be covered with a suitable surface coating;

two of the interfaces located in the vicinity of one another are separated from one another, preferably the second interface and the fourth interface are independent of one another;

alternatively, two of the interfaces located in the vicinity of one another are associated, coupled or consolidated together, preferably the first interface and the third interface are produced, secured or merged into a common interface body.

The invention also relates to a ventilation assembly that can be used in a contaminated environment, in particular an NRBC environment, comprising a medical ventilator, also called breathing assistance apparatus, around which a protective cover according to the invention is sealably arranged.

According to the considered embodiment, the ventilation assembly of the invention can comprise one or more of the following features:

a patient circuit is connected to the first connection interface of the cover;

the patient circuit that is connected to the first connection interface comprises at least one gas hose, in particular a flexible pipe or similar;

the patient circuit comprises at least one gas hose fluidly connected to a breathing interface, in particular to a breathing mask or similar;

an air purification device, preferably a filtration device, is connected to the second connection interface of the cover;

the air purification device comprises a filtration cartridge that is designed and adapted for use in a contaminated environment of the NRBC or similar type;

the air purification device comprises a filtration cartridge configured to retain and/or eliminate particles and/or pollutants in solid, liquid and/or gaseous form;

the purification device comprises a filtration cartridge comprising at least one anti-particulate filter for eliminating solid and/or aerosol particles, and/or at least one active carbon or similar filter for eliminating gaseous pollutants.

The invention also relates to a ventilation assembly that can be used in a contaminated environment, in particular an NRBC environment, comprising a medical ventilator, around which a protective cover according to the invention is sealably arranged.

The protective cover according to the invention is installed around the ventilator prior to intervention in an NRBC environment, i.e. in a non-contaminated location. The cover provides protection by virtue of its impermeability, in particular at the inlets and outlets of the ventilator, and does so during its operation but also when it is stopped and between possible changes of patient, as well as during decontamination.

According to the considered embodiment, the ventilation assembly of the invention can comprise one or more of the following features:

the protective cover is detachably mounted around the medical ventilator;

the protective cover comprises a peripheral casing comprising a first, a second and a fourth connection interface, and optionally a third connection interface;

the first connection interface comprises a gas inlet fluidly connected to a gas outlet of the medical ventilator;

the second connection interface comprises a free gas outlet leading into the internal compartment of the cover;

the fourth connection interface comprises an oxygen outlet fluidly connected to an oxygen inlet of the medical ventilator;

the third connection interface comprises a gas inlet fluidly connected to a PEP pressure outlet arranged on a medical ventilator and/or a gas outlet fluidly connected to a PEP pressure control line;

the first connection interface is fluidly connected to a patient circuit;

the second connection interface is fluidly connected to an air purification device, preferably a filtration device;

the fourth connection interface is fluidly connected to an oxygen supply line, preferably an oxygen supply line supplied with oxygen by an oxygen container, in particular an oxygen bottle;

the medical ventilator is a breathing assistance apparatus able and designed to deliver gas to the patient, i.e. to deliver valve-controlled ventilation enabling simple ventilation to be provided at a single pressure level (i.e. CPAP) or at a double pressure level (i.e. BiPAP, VSAI), with control of the inhaled and exhaled volumes, according to the needs of the patient;

the medical ventilator comprises a frame or external shell;

the medical ventilator comprises a motorized micro-blower, also called turbine or compressor, allowing air or oxygen-enriched air to be sucked in and supplied to the patient circuit, for example, a flexible gas hose or similar supplying a patient breathing interface, such as a breathing mask or similar;

the medical ventilator comprises a micro-blower comprising an electric motor, preferably a brushless motor, arranged in a rigid peripheral housing that is designed to reach a rotation speed of up to 70000 rpm or more;

the micro-blower of the medical ventilator comprises an electric motor rotating a rotary shaft supporting a bladed wheel;

the micro-blower of the medical ventilator comprises an internal wheel compartment of a volute surmounting the motor, inside which compartment the bladed wheel is arranged so as to be rotationally movable therein;

it comprises electronics for controlling the ventilation, for example, a microprocessor electronic board and/or a human-machine interface (HMI).

Furthermore, the invention also relates to a ventilation system comprising:

a ventilation assembly according to the invention comprising a medical ventilator, around which a protective cover is arranged;

a patient circuit comprising a flexible gas hose provided with a breathing interface, said flexible gas hose being fluidly connected to the first connection interface of the protective cover; and an oxygen supply line supplied with oxygen by an oxygen container, in particular an oxygen bottle, and fluidly connected to the fourth connection interface of the protective cover.

Preferably, the ventilation system also comprises a PEP pressure control line.

BRIEF DESCRIPTION OF THE DRAWINGS

The invention will now be better understood by virtue of the following detailed description, which is provided by way of a non-limiting illustration, and with reference to the appended figures, in which.

DETAILED DESCRIPTION OF PREFERRED EMBODIMENTS

Figure 1:
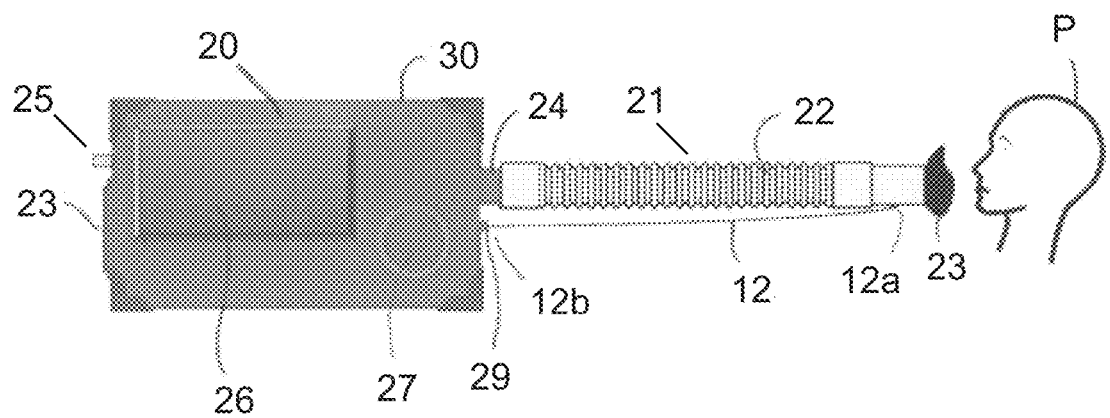
FIG. 1 depicts a medical ventilator that can be used for emergency treatment of a patient suffering from respiratory failure.

FIG. 1 depicts a medical ventilator 20 that can be used for emergency treatment of a patient P suffering from respiratory failure, for example, an apparatus delivering gas at one or more pressure levels, i.e. of the CPAP, BPAP, VSAI, CPV or other type.

It comprises an external frame or shell 30 containing the various components ensuring proper operation of the medical ventilator 20. Thus, the frame 30 of the medical ventilator 20 contains a motorized micro-blower, also called turbine or compressor, allowing air or oxygen-enriched air to be sucked in and supplied to the patient circuit 21, for example, a flexible gas hose 22 or similar supplying a patient breathing interface 23, such as a breathing mask or similar. The flexible gas hose 22 of the patient circuit 21 is fluidly connected to a gas outlet connector 24 supported by the frame 30 of the ventilator 20, by screwing, interlocking or other.

The motorized micro-blower comprises an electric motor arranged in a rigid peripheral casing used to protect the motor, i.e. typically the stator and the rotor of the motor. Preferably, the electric motor is brushless and/or is designed to reach a rotation speed that is typically of the order of 30,000 to 40,000 rpm, even up to 70,000 rpm or even above. During operation, the motor of the micro-blower rotates a rotary shaft, thus called 'axis', supporting a bladed wheel, also called 'vane wheel'. This bladed wheel preferably has a circular section with a diameter that is between 20 and 80 mm, typically between 30 and 60 mm. The bladed wheel is arranged so as to be rotationally movable inside the internal wheel compartment of a volute surmounting the electric motor and the housing, so as to generate the gaseous flow at a pressure that is above the atmospheric pressure (>1 atm) that is sent to the patient P.

The volute can be formed by two semi-volutes, namely a lower semi-volute and an upper semi-volute, securely and sealably assembled and attached together, for example, by bonding or other means. A seal can be interposed between these semi-volutes. The volute has a generally circular section and further comprises a central gas inlet, through which the gas is sucked into the internal wheel compartment located in the volute during wheel rotations, and a gas flow outlet, through which the gas flow generated in the wheel compartment, during wheel rotations, exits the micro-blower, before being subsequently directed to the patient circuit 21.

The micro-blower is fluidly connected to the patient circuit 21 via an internal gas circuit, namely one or more gas passages arranged in the frame 30 supplied by the gas flow outlet of the volute.

The suction of air by the micro-blower occurs via an opening 23 arranged in the frame 30 and an internal air-routing passage connecting the opening 23 to the inlet of the volute of the micro-blower.

When a mixture of air and of oxygen, i.e. air/$O_2$, has to be supplied to the patient, the air/$O_2$ mixing generally occurs upstream of the inlet of the volute of the micro-blower. The oxygen enters the frame 30 via an oxygen inlet connector 25 allowing a fluid connection to be made with a flexible hose supplied by an oxygen source, for example, a gas bottle or similar.

The frame 30 of the medical ventilator 20 also contains control means, for example, a microprocessor electronic board, such as a microcontroller, particularly allowing the operation of the micro-blower to be controlled, namely acceleration and deceleration phases, and means for supplying electric current, such as one or more rechargeable batteries or similar for supplying electric current to the various components of the ventilator 20 requiring electric current to operate, in particular to the control means and to the micro-blower, via a suitable connector, such as cables or electric circuits.

Furthermore, the medical ventilator 20 also comprises a display interface 26, such as a screen or similar, allowing information, warnings, curves and/or any other information or data that is useful for the user, typically the caregivers or any other person, to be displayed, and/or a human-machine interface (HMI) allowing the user to implement start-up or shutdown of the ventilator, adjustments, changes of ventilation mode, warning acknowledgements, confirmations of selections, etc. Thus, the HMI can comprise one or more buttons, keys, cursors, numerical keypads, keyboards, etc., for example, a rotary selection knob 27.

Furthermore, the medical ventilator 20 also comprises a PEP pressure control line 12, such as a small flexible hose, connected close to the patient P, for example, in the immediate vicinity and upstream of the breathing interface 23. The PEP pressure control line 12 comprises, at one of its ends, a PEP pressure supply port and, at its other end, a connection connector 12b for fluidly connecting it to the ventilator 20 via a pressure-tapping connector 29 in fluid communication with an internal pressure measurement circuit arranged in the ventilator 20 and leading to a pressure sensor. The connection is implemented by screwing, bayonet fitting or other, for example.

Figure 2:
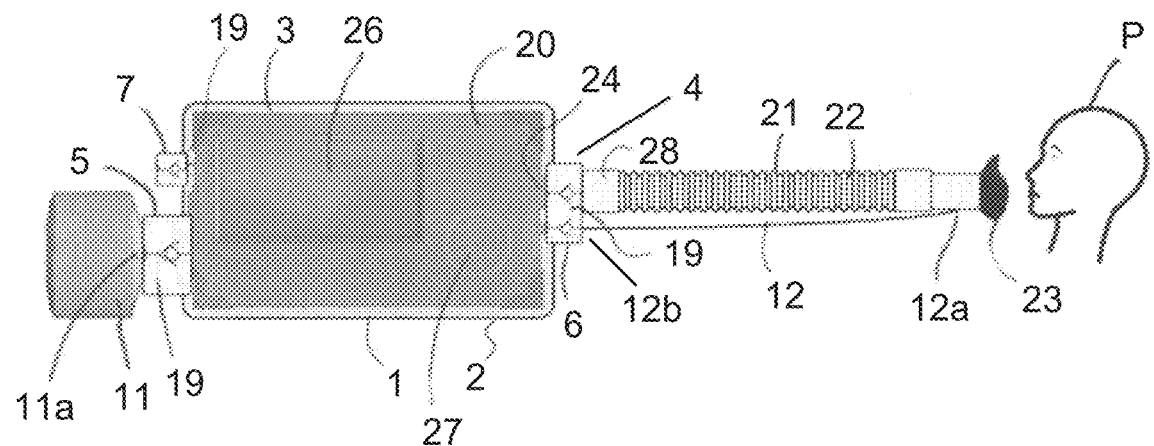
FIG. 2 depicts the medical ventilator of FIG. 1 equipped with a flexible protective cover according to the invention.

In order to allow assisted ventilation of a patient to be implemented in a contaminated environment, in particular of the NRBC type, with such a ventilator 20, whilst protecting the medical ventilator 20 and subsequently allowing this medical ventilator 20 to be reused, i.e. to avoid difficult decontamination of the ventilator, or worse, having to discard the ventilator, according to the present invention, it is proposed for the ventilator 20 to be equipped with a particular protective cover 1, as shown in FIG. 2.

The medical ventilator 20 that must be equipped with the cover 1 is advantageously portable or wearable, i.e. it is of a reasonable weight and size and is able to be carried by a user, for example, it weighs less than approximately 6 kg, and the width of the frame 30 is between approximately 25 and 40 cm, it is between approximately 10 and 15 cm deep, and it is between approximately 20 and 30 cm high.

More specifically, according to the invention, the protective cover 1 comprises, as shown in FIG. 2, a flexible peripheral casing 2 surrounding the medical ventilator 20 and defining an internal compartment 3, i.e. a space or volume, that is designed to accommodate the medical ventilator 20. Advantageously, the size of the internal compartment 3 of the cover 1 is greater than or equal to the size of the ventilator 20 that is arranged therein, i.e. schematically the dimensions of the frame 30 of the ventilator 20.

The peripheral casing 2 comprises opening/closing means (not shown) allowing access to be granted to the internal compartment 3 of the cover 1 for the insertion or extraction of the medical ventilator 20, then to allow the cover 1 to be hermetically closed, i.e. in a sealed manner, when the cover 1 is hermetically closed, so that pollutants cannot enter therein, even in an NRBC environment. The opening/closing means comprise, for example, a zip or similar fastener, such as a hook-and-loop strip.

According to the invention, the peripheral casing 2 also comprises a plurality of connection interfaces 4, 5, 6, 7 sealably attached to said peripheral casing 2, i.e. pollutant ingress is not possible at the connection interfaces 4, 5, 6, 7, particularly between the external structure of the connection interfaces 4, 5, 6, 7 and the wall of the peripheral casing 2 of the cover 1. They are attached, for example, by bonding, thermobonding/thermosoldering or mechanically by clamping parts and seals.

More specifically, the peripheral casing 2 comprises a first, a second, a third and a fourth connection interface 4, 5, 6, 7.

The first connection interface 4 allows fluid connection of the patient circuit 21, typically a flexible gas hose 22, supplying the breathing interface 23 supplying the gas to the patient P. The flexible gas hose 22 comprises an attachment connector 28 allowing the flexible gas hose 22 to be secured to the first connection interface 4, for example, by screwing, bayonet fitting or other.

The second connection interface 5 allows fluid connection of an air purification device 11, such as a filtration cartridge that is designed and adapted for use in a contaminated environment of the NRBC type, which device is configured to retain and/or eliminate particles and/or pollutants in solid, liquid and/or gaseous form. For example, the filtration cartridge comprises an anti-particulate filter for eliminating solid and/or aerosol particles, and/or active carbon or similar for eliminating gaseous pollutants. The air purification device 11 comprises connection means 11a, for example, by screwing, bayonet fitting, by interlocking or other, allowing it to be sealably secured to the second connection interface 5.

The third connection interface 6 allows fluid connection of the PEP pressure control line 12 used to modulate the expiratory pressure or PEP of the patient P.

According to the selected embodiment, two interfaces located in the vicinity of one another can be separated from one another, as shown in FIG. 2 for the second interface 5 and the fourth interface 7, which are independent of one another or, conversely, can be associated, coupled or consolidated together, as shown in FIG. 2 for the first interface 4 and the third interface 6, which are secured or merged into a common interface body 19.

The fourth connection interface 7 allows fluid connection of an oxygen supply line, for example, a flexible pipe supplied by an oxygen source (not shown), for example, a gas bottle or similar. The connection of the oxygen supply line in this case also occurs via a suitable connector, for example, by screwing, bayonet fitting or other.

According to the invention, the connection interfaces 4, 5, 6, 7 each comprise an internal gas passage 14, i.e. each connection interface 4, 5, 6, 7 comprises an interface body 19 traversed by an internal gas passage 14 fluidly connecting the inside 3 and the outside of the peripheral casing 2 of the cover 1.

The interface bodies 19 of the connection interfaces 4, 5, 6, 7 are formed by a semi-rigid material of the thermoplastic polymer type, for example, ABS, PA or similar, or elastomer, for example, polyurethane, silicon or similar.

Figure 3:
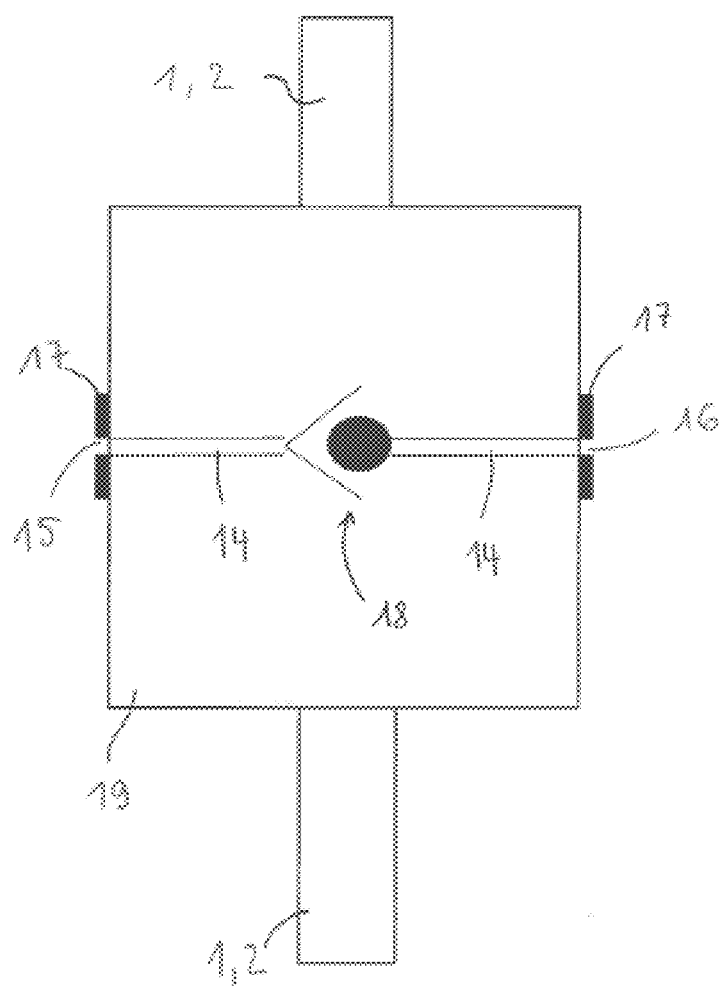
FIG. 3 schematically shows a connection interface arranged in the flexible protective cover according to the invention.

As shown in FIG. 3, the internal gas passages 14 traversing the interface bodies 19 of the connection interfaces 4, 5, 6, 7 each comprise a gas inlet 15 and at least one gas outlet 16, i.e. gas inlet and outlet orifices allowing gas to enter and subsequently exit said internal gas passages 14, therefore to be routed through the connection interfaces 4, 5, 6, 7.

Furthermore, at least one sealing device 18 is provided that is preferably arranged in each internal gas passage 14 in order to normally seal each internal gas passage 14 of the connection interfaces 4, 5, 6, 7, i.e. when the connection interfaces 4, 5, 6, 7 are not used and no gas supply line, PEP pressure control line 12 or purification device 11 is connected thereto. By default, the sealing devices 18 seal the internal gas passages 14 of the connection interfaces 4, 5, 6, 7 so as to prevent any circulation of gas therein, in particular to prevent any gas entering the internal compartment 3 of the casing 2 of the cover 1.

The sealing devices 18 preferably are non-return valves that are normally closed to prevent any gas circulation, particularly to prevent the ingress of contaminated air into the internal gas passages 14 in which these non-return valves are installed. They are therefore only opened to allow gas to pass through when the inlet and/or the outlet of the connection interfaces 4, 5, 6, 7 are fluidly connected to the oxygen line, to the patient circuit 21, the PEP pressure control line 12 and/or to the air purification device 11.

According to another embodiment, it is also possible to use, instead of and/or in addition to sealing devices 18, one or more detachable plugs or lids that are sealably attached to the gas inlet of the internal gas passages 14 of one or more of the connection interfaces 4, 5, 6, 7, so as to seal them in the absence of a connection. Such plugs or lids can be useful during prolonged storage and/or during disinfection of the equipment.

The interface bodies 19 are also provided with connection interfaces 4, 5, 6, 7 for the connection means 17, by screwing, interlocking or other, allowing mechanical and fluid connection thereto, on the one hand, of the oxygen supply line, the patient circuit 21, the PEP pressure control line 12 and the air purification device 11 and, on the other hand, of the PEP pressure connector 29 of the ventilator 20, the oxygen inlet connector 25 and the gas outlet 24.

It is to be noted that the inlet 23 of the ventilator 20 is not necessarily connected to the second connection interface 5, but can simply lead into the internal compartment 3 of the casing 2 in order to suck in the air that is located therein, during the operation of the micro-blower.

Furthermore, the cover 1 is partly or completely made of transparent flexible material, i.e. it is completely transparent or indeed opaque but has transparent sections, such as windows or similar, allowing a user to see the ventilator 20 that is arranged in the cover 1, particularly to be able to read or see the information, data, curves, warnings or other information displayed on the display screen 26 of the ventilator 20 or HMI 27. Advantageously, the cover 1 is made up of PVC or similar.

Preferably, the protective cover 1 of the invention is at least IP67 rated and is designed to withstand severe environmental stresses, in particular high temperatures, abrasion and tearing, as well as chemical substances.

Of course, the cover can also be provided with strengtheners, such as feet, "bumper" elements, etc., particularly in its lower portion, which is in contact with the ground, so as to improve its resistance to impacts, abrasions, scrapes or similar, caused by frequent contact with the ground or with any other surface.

In general, a medical ventilator 20 equipped with a protective cover 1 according to the invention can be used for emergency treatment of one or more patients suffering from respiratory failure in a contaminated environment or area of the NRBC type, particularly in the event of a conflict, an attack or an industrial accident.

What is claimed is:

1. A protective cover (1) for a medical ventilator (20) adapted for use in a contaminated environment, comprising a peripheral casing (2) defining an internal compartment (3) designed to accommodate a medical ventilator (20), wherein:
    the peripheral casing (2) comprises a plurality of connection interfaces (4, 5, 6, 7) sealably attached to said peripheral casing (2), comprising:
        a first connection interface (4) allowing fluid connection of a patient circuit (21); and
        a second connection interface (5) allowing fluid connection of an air purification device (11);
    and each connection interface (4, 5, 6, 7) comprises at least one internal gas passage (14) with at least one gas inlet (15) and at least one gas outlet (16);
    characterized in that at least one sealing device (18) is arranged in the at least one internal gas passage (14) of at least one connection interface (4, 5, 6, 7) for sealing said at least one internal gas passage (14).

2. The protective cover according to claim 1, characterized in that at least one sealing device (18) is arranged in the at least one internal gas passage (14) of each connection interface (4, 5, 6, 7).

3. The protective cover according to claim 2, characterized in that at least one sealing device (18) is a non-return valve.

4. The protective cover according to claim 1, characterized in that at least one portion of the peripheral casing (2) is formed by at least one transparent polymer material.

5. The protective cover according to claim 1, further comprising:
    a third connection interface (6) allowing fluid connection of a Positive Expiratory Pressure (PEP) pressure control line (12); and/or
    a fourth connection interface (7) allowing fluid connection of an oxygen supply line.

6. A ventilation assembly (1, 20) that can be used in a contaminated environment, comprising a medical ventilator (20), around which a protective cover (1) according to claim 5 is sealably arranged.

7. The ventilation assembly according to claim 6, characterized in that the protective cover (1) comprises the peripheral casing (2) comprising the first (4), the second (5) and the fourth (7) connection interface, wherein:
    the first connection interface (4) comprises a gas inlet (15) fluidly connected to a gas outlet (24) of the medical ventilator (20);
    the second connection interface (5) comprises a free gas outlet (16) leading into the internal compartment (3) of the casing (2); and/or
    the fourth connection interface (7) comprises an oxygen outlet (16) fluidly connected to an oxygen inlet (25) of the medical ventilator (20).

8. The ventilation assembly according to one of claim 7, characterized in that:
    the first connection interface (4) is fluidly connected to a patient circuit (21);
    the second connection interface (5) is fluidly connected to an air purification device (11); and/or
    the fourth connection interface (7) is fluidly connected to an oxygen supply line.

9. A ventilation system (1, 20, 21) comprising:
    the ventilation assembly according to claim 6, comprising a medical ventilator (20), around which a protective cover (1) is arranged;
    a patient circuit (21) comprising a flexible gas hose (22) provided with a breathing interface (23), said flexible gas hose (22) being fluidly connected to the first connection interface (4) of the protective cover (1); and
    an oxygen supply line supplied with oxygen by an oxygen container fluidly connected to the fourth connection interface (7) of the protective cover (1).

10. The protective cover as claimed in claim 1, characterized in that the plurality of connection interfaces (4, 5, 6, 7) are formed by at least one semi-rigid material.

* * * * *